(12) United States Patent
Dirauf et al.

(10) Patent No.: US 10,993,695 B2
(45) Date of Patent: May 4, 2021

(54) PORTABLE EXPANSION UNIT FOR OPERATING A MEDICAL DEVICE, AND METHOD FOR OPERATING A MEDICAL DEVICE

(71) Applicant: SIEMENS HEALTHCARE GMBH, Erlangen (DE)

(72) Inventors: Franz Dirauf, Ebensfeld (DE); Robert Kagermeier, Nuremberg (DE); Joerg Hofmann, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 305 days.

(21) Appl. No.: 15/813,784

(22) Filed: Nov. 15, 2017

(65) Prior Publication Data

US 2018/0206818 A1 Jul. 26, 2018

(30) Foreign Application Priority Data

Jan. 24, 2017 (EP) ..................................... 17152779

(51) Int. Cl.
*A61B 8/00* (2006.01)
*G05B 19/042* (2006.01)
(Continued)

(52) U.S. Cl.
CPC .............. *A61B 8/4427* (2013.01); *A61B 6/10* (2013.01); *A61B 6/467* (2013.01); *A61B 8/467* (2013.01);
(Continued)

(58) Field of Classification Search
CPC .... G08C 2201/63; G08C 25/00; A61B 6/548; G08B 29/16; H04B 1/00; H04L 1/08;
(Continued)

(56) References Cited

U.S. PATENT DOCUMENTS

| 5,792,201 A * | 8/1998 | Causey, III | .............. | A61N 1/37 607/27 |
| 6,893,395 B1 * | 5/2005 | Kraus | ................ | A61N 1/37276 600/300 |

(Continued)

FOREIGN PATENT DOCUMENTS

| CN | 102077545 A | 5/2011 |
| CN | 104919464 A | 9/2015 |

(Continued)

*Primary Examiner* — Mirza F Alam
(74) *Attorney, Agent, or Firm* — Laurence Greenberg; Werner Stemer; Ralph Locher

(57) ABSTRACT

A portable expansion unit controls safety-relevant functions of a medical device. The expansion unit has a retaining device to be adjusted to the size of a flat, portable operating unit of the medical device. The retaining device mechanically connects the expansion unit detachably with the portable operating unit. A communication module establishes a safety-related data connection with the medical device. This combines a mobile, portable consumer operating device, such as a tablet computer or smartphone, which does not fulfill any particular safety-related requirements, with an expansion unit, which permits the control of safety-relevant functions with the aid of a safety-related radio protocol.

20 Claims, 2 Drawing Sheets

(51) Int. Cl.
  *G06F 3/01* (2006.01)
  *G16H 40/67* (2018.01)
  *G06F 1/16* (2006.01)
  *A61B 6/00* (2006.01)
  *A61B 6/10* (2006.01)
  *G06F 19/00* (2018.01)
  *A61B 1/04* (2006.01)
  *G06Q 50/22* (2018.01)

(52) U.S. Cl.
  CPC ......... *G05B 19/042* (2013.01); *G06F 1/1626* (2013.01); *G06F 1/1632* (2013.01); *G06F 1/1669* (2013.01); *G06F 1/1671* (2013.01); *G06F 3/01* (2013.01); *G06F 19/3418* (2013.01); *G16H 40/67* (2018.01); *A61B 1/04* (2013.01); *A61B 8/4209* (2013.01); *A61B 8/4405* (2013.01); *A61B 8/4433* (2013.01); *G06Q 50/22* (2013.01)

(58) Field of Classification Search
  CPC .. H04L 12/417; H04W 24/04; G06F 11/0793; G06F 21/85
  See application file for complete search history.

(56) References Cited

U.S. PATENT DOCUMENTS

| | | | |
|---|---|---|---|
| 7,073,083 | B2* | 7/2006 | Litwin, Jr. .......... G06F 11/0745 709/205 |
| 8,391,782 | B2 | 3/2013 | Holstegge et al. |
| 2002/0003812 | A1* | 1/2002 | Haartsen ............... H04L 1/0061 370/474 |
| 2006/0066438 | A1* | 3/2006 | Altounian ............... G06F 21/86 340/5.53 |
| 2007/0055116 | A1 | 3/2007 | Clark et al. |
| 2009/0062937 | A1 | 3/2009 | Holstegge et al. |
| 2010/0094130 | A1* | 4/2010 | Ninomiya ................ A61B 8/00 600/437 |
| 2011/0119074 | A1 | 5/2011 | Drucker et al. |
| 2011/0145894 | A1 | 6/2011 | Garcia Morchon et al. |
| 2012/0109688 | A1 | 5/2012 | Yoo |
| 2016/0028874 | A1 | 1/2016 | Mankopf et al. |

FOREIGN PATENT DOCUMENTS

| | | |
|---|---|---|
| DE | 102008060117 A1 | 6/2010 |
| EP | 2034463 A2 | 3/2009 |
| JP | 2012522450 A | 9/2012 |
| KR | 1020030058711 A | 7/2003 |
| KR | 1020140107806 A | 9/2014 |

* cited by examiner

PORTABLE EXPANSION UNIT FOR OPERATING A MEDICAL DEVICE, AND METHOD FOR OPERATING A MEDICAL DEVICE

CROSS-REFERENCE TO RELATED APPLICATION

This application claims the benefit, under 35 U.S.C. § 119, of European patent application EP17152779.9, filed Jan. 24, 2017; the prior application is herewith incorporated by reference in its entirety.

BACKGROUND OF THE INVENTION

Field of the Invention

The invention relates to a portable expansion unit, which is set up to control safety-relevant functions of medical devices. The invention also relates to an associated method for operating a medical device.

The operation of medical devices is also to be designed to be up-to-date and therefore intuitive, clear and user-friendly. The user interfaces of mobile tablet computers and smartphones have become widely established and are the standard which is not only accepted and understood by the users but has already been extended to wide areas of daily life with the aid of apps and HTML representation.

This type of user interface with an animated graphical display, touch function and additional sensor technology, such as inclination and acceleration sensors, cameras etc., is also particularly well suited to operating medical devices.

However, consumer devices do not fulfill the requirements which are to be fulfilled for safety-relevant functions in medical technology, such as motion control, radiation release etc. These functions must be controlled in such a way that they are not unintentionally released on account of a simple hardware or software error and can thus do damage ("initial system error").

Previously only specially developed operating devices were used, which often only permit simple and less intuitive operating functions and are comparatively expensive due to their limited numbers.

BRIEF SUMMARY OF THE INVENTION

It is accordingly an object of the invention to provide a portable expansion unit for operating a medical device, and a method for operating a medical device, which overcome the above-mentioned and other disadvantages of the heretofore-known devices and methods of this general type and to adapt commercially available and very cost-effective mobile, portable consumer operating devices, such as tablet computers and smartphones, for operating medical devices.

With the foregoing and other objects in view there is provided, in accordance with the invention, a portable expansion unit for controlling safety-relevant functions of a medical device, the expansion unit comprising:

a retaining device to be adjusted to a size of a flat, portable operating unit of the medical device, said retaining device being configured to mechanically connect the expansion unit detachably with the portable operating unit; and a communications module configured to establish a safety-related data connection with the medical device.

In accordance with the invention, the operation of safety-relevant functions is delegated to an external additional unit (=expansion unit), which is qualified in accordance with the relevant rules and standards (keyword "initial system error"). The mobile operating device (=portable operating unit) itself is thus not subject to the safety-related requirements. The typically very short model cycles with consumer operating devices of this type therefore no longer present any problems with respect to qualification and permission.

In accordance with the invention, an expansion unit is specified for the wireless execution of safety-relevant functions during the operation of medical devices. The expansion unit can be combined with commercially available, flat portable computers (tablets), such as tablet computers, smartphones, etc. In such cases the expansion unit is mechanically connected to the portable operating unit by means of a variable retaining device which can be adjusted to the size of the portable operating device (for instance can be clamped with the aid of a lever or is equipped with a spring balancer) or a bracket.

The expansion unit is connected via a radio connection or also by a cable connection to a receiver module of the medical device. A secured protocol with a detection of transmission errors and timeouts is transmitted via the digital communication, e.g., with Bluetooth or WLAN.

The invention claims a portable expansion unit, which is set up to control, trigger or release, for instance, safety-relevant functions of medical devices. To this end the novel device comprises a retaining device which can be adjusted to the size of a flat, portable operating unit of the medical device, said retaining device being embodied to mechanically connect the expansion unit detachably to the operating unit, and a (first) communication module, which is embodied to establish a safety-related data connection with the medical device.

The advantage of the invention consists in combining a mobile, portable consumer operating device, such as a tablet computer or smartphone, which does not fulfill any particular safety-related requirements, with an expansion unit, which permits a control of safety-relevant functions with the aid of a safety-related radio protocol.

In one development, the retaining device can be embodied to clamp the expansion unit from the underside of the operating unit to the operating unit.

In a further embodiment, the retaining device has a displaceable lever which can be fixed continuously in the retaining device, and is embodied to clamp the operating unit in the expansion unit.

In one optional embodiment, the retaining device has a displaceable lever with a spring balancer, which is embodied to clamp the operating unit into the expansion unit.

In a further design, the underside of the expansion unit can be embodied to be flat such that the expansion unit connected to the operating unit can be placed on a flat surface in the manner of a desk.

In one development, the first communication module can be embodied to set up a Bluetooth or WLAN connection.

In a further embodiment, the expansion unit can have a second communication module, which is embodied to exchange data with the operating unit.

Furthermore, the second communication module can be connected to the operating unit by way of NFC or USB.

In one development, the expansion unit can have an operating field which faces a user during operation and which is embodied to project beyond the operating unit when the expansion unit is mechanically connected to the operating unit.

In a further embodiment of the invention, the operating field can have a touch screen or a keypad.

In a preferred embodiment, the operating unit can be a tablet computer or a smartphone.

In one development, at least one key button can be arranged on the retaining device, which can be triggered by a user of the expansion unit using the hand which is holding the expansion unit.

With the above and other objects in view there is also provided, in accordance with the invention, a method for operating a medical device, wherein safety-relevant functions of the operation of the medical device are triggered by an inventive expansion unit.

Other features which are considered as characteristic for the invention are set forth in the appended claims.

Although the invention is illustrated and described herein as embodied in a portable expansion unit for operating a medical device, and a method for operating a medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF AN EXEMPLARY EMBODIMENT

Figure 1:
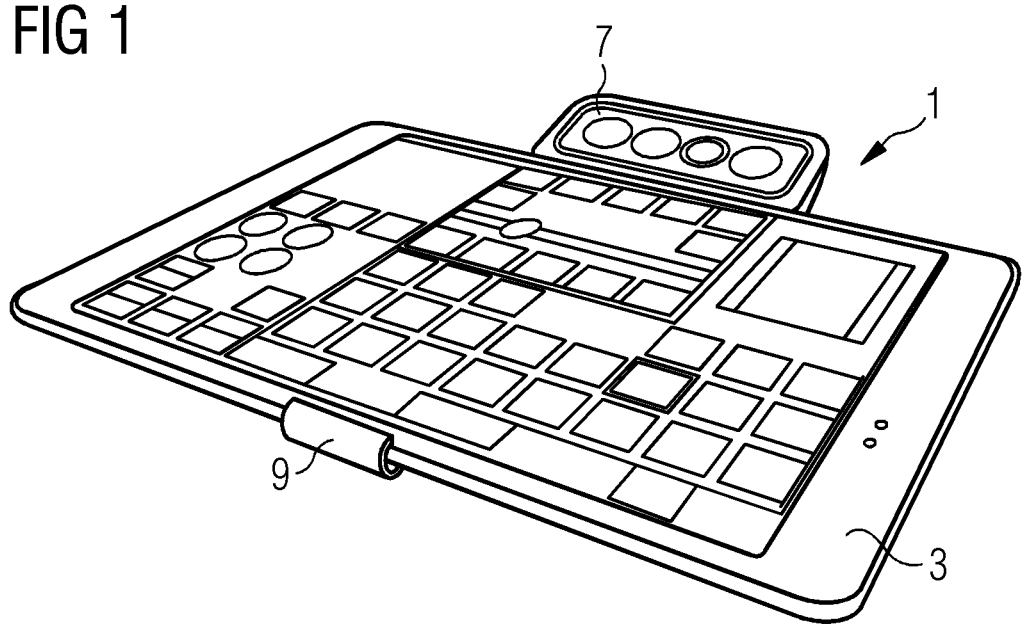
FIG. 1 is a top perspective of an expansion unit on a tablet computer.

Referring now to the figures of the drawing in detail and first, particularly, to FIG. 1 thereof, there is shown a portable expansion unit 1, which is fastened to a portable, flat operating unit 3 (a commercially available tablet computer, for instance). The expansion unit 1 surrounds the rear side of the operating unit 3 in the manner of a bracket. To this end, it has a retaining device, with a claw-shaped end 9 which is shown. The claw 9 embraces the edge of the operating unit 3. All parameters of a medical device are set and non-safety relevant functions are controlled with the aid of the operating unit 3.

The operating field 7 of the expansion unit 1 is also shown, with the aid of which safety-relevant functions of a medical device (for instance an x-ray trigger) can be controlled. The operating field 7 can be embodied as a touch screen or as a keypad, for instance. It projects beyond the operating unit 3, so that it is easily visible and operable.

Figure 2:
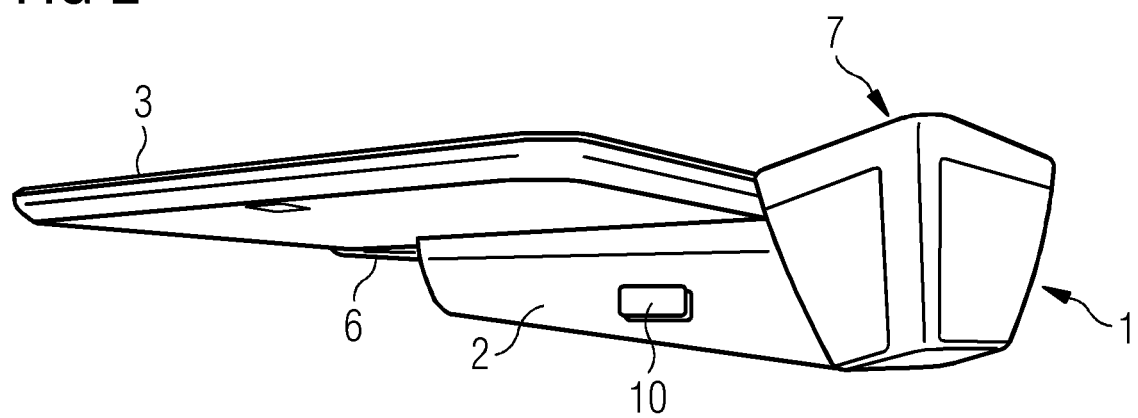
FIG. 2 is a bottom perspective of an expansion unit on a tablet computer.
Figure 3:
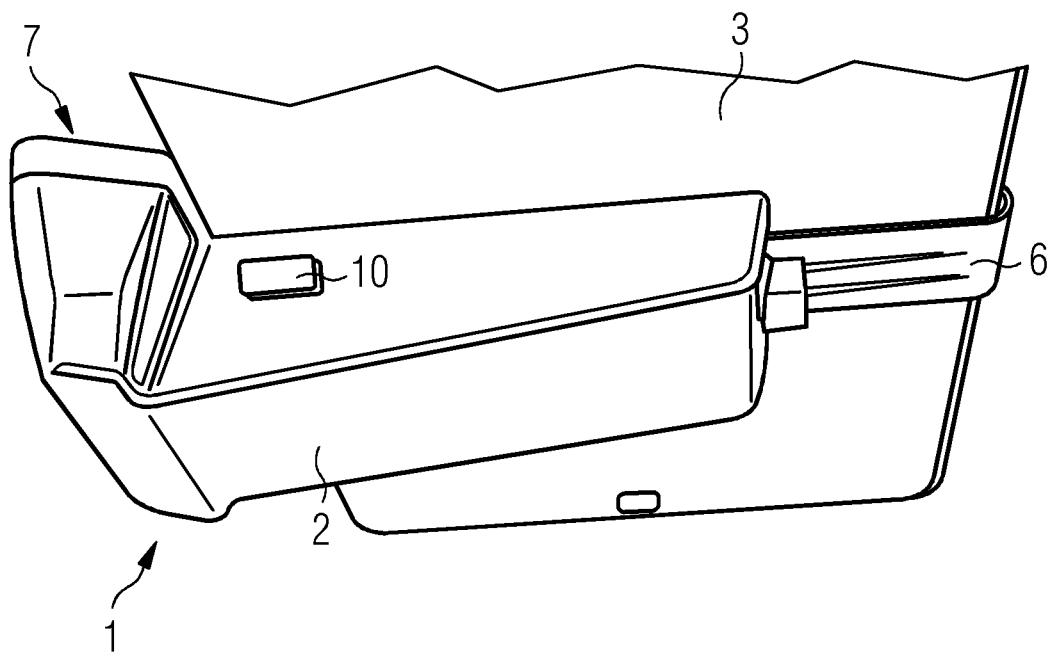
FIG. 3 is a detailed view of the retaining device of an expansion unit.

FIG. 2 and FIG. 3 show the arrangement in FIG. 1 from below. The expansion unit 1 is detachably fastened to the operating unit 3 from the rear side of the operating unit 3 with the aid of the retaining device 2. To this end, the retaining device 2 has a lever 6, which can be embodied as a locking lever or as a spring balancer. As a result, the expansion unit 1 is clamped to the operating unit 3.

The underside of the housing of the retaining device 2 is flat and beveled, so that the operating unit 3 can be placed on a flat surface in a secure and shake-free manner. The expansion unit 1 therefore acts a desk for the operating unit 3.

A keyboard 10, which permits a single-handed actuation with the hand holding the expansion unit, may also be arranged on the retaining device 2.

Figure 4:
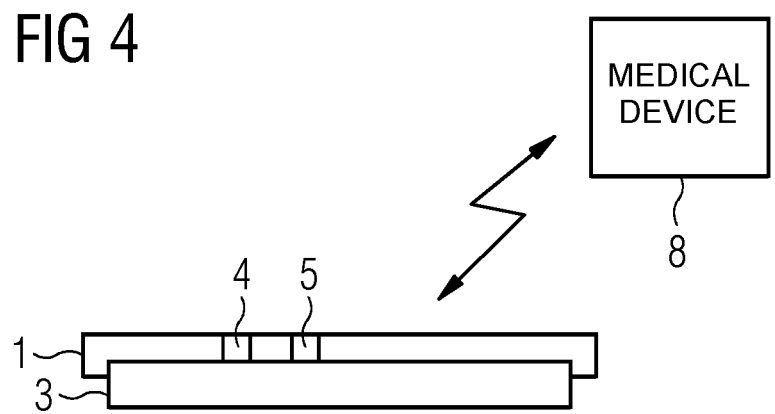
FIG. 4 is a block diagram of an arrangement with an expansion unit and a medical device.

FIG. 4 shows a block diagram of an arrangement with an expansion unit 1 and a medical device 8. The expansion unit 1 has a first communication module 4 and a second communication module 5. A secure data connection, for instance by way of Bluetooth or WLAN, can be set up via the first communication module 4 to the medical device 8. The second communication module 5 can be used to communicate with the operating unit 3 via NFC or USB.

The expansion unit 1 has the following properties and functions:

In accordance with regulatory provisions to be fulfilled, it also permits safety-relevant functions, such as movements or radiation release of medical devices 8, to be wirelessly controlled by keystroke.

If necessary, an emergency stop function can also be realized, wherein the emergency stop switch signals to the user via a colored display whether he is currently active or inactive, i.e. whether or not a safety-related communication connection currently exists.

The assignment between an operating unit 3, such as a tablet computer or smartphone, to an expansion unit 1 can be fixedly assigned by way of allocating ID codes. Alternatively, the assignment can also be carried out automatically by way of a near field radio connection (e.g. NFC) or by way of a wired communication (e.g. USB or Audio Interface).

In order to ensure the data security of important setting parameters, the expansion unit 1 can check the consistency of these parameters, before a safety-relevant function, such as a movement or radiation, can be released by a keypress on the operating field 7. For this purpose, the expansion unit 1 receives the desired setting parameters from the operating unit 3, e.g. via a near field radio connection or a wired communication. The expansion unit 1 receives the actually set parameters from the medical device 8 via the secure radio connection. The respective function will only be released when there is a match between the parameters which are desired and the parameters which are set on the medical device 8.

The expansion unit 1 can be registered by suitably encoding the wireless communication (with the aid of the first communication module 4) and the allocation of ID codes to one or a number of medical devices 8, in order to operate the same.

Provided the expansion unit 1 is registered to a number of devices 8, the user can select on the user interface of the operating unit 3 which registered medical device 8 he would like to operate. The user interface of the operating field 7 is then automatically adjusted to the requirements of the respective device 8. Alternatively, the device 8 to be operated can be selected by way of a wireless communication by means of near field radio connection (e.g. NFC).

The shaping of the expansion unit 1 is designed such that it is held together with the operating unit 3 or securely from below with the fingers of one hand and can be easily operated with the other hand.

On account of the beveled shape of the expansion unit 1, the operating unit 3 is placed into a desk position when positioned on a table so that the operation can be carried out in a very ergonomic and user-friendly manner.

Although the invention has been illustrated and described in detail based on the preferred exemplary embodiments, the invention is not restricted by the examples given and other variations can be derived therefrom by a person skilled in the art without departing from the protective scope of the invention.

The following is a summary list of reference numerals and the corresponding structure used in the above description of the invention:

1 Expansion unit
2 Retaining device
3 Operating unit
4 First communication module
5 Second communication module
6 Lever of the retaining device 2
7 Operating field of the expansion unit 1
8 Medical device
9 Collar-shaped end of the lever 6
10 Button

The invention claimed is:

1. A portable expansion unit for controlling functions of a medical device, the expansion unit comprising:
a retaining device to be adjusted to a size of a flat, portable operating unit of the medical device, said retaining device being configured to mechanically connect the expansion unit detachably to the portable operating unit, the, portable operating unit being a tablet computer or a smartphone; and
a first communication module configured to establish a data connection with the medical device to control at least one function selected from the group consisting of triggering a release of radiation from the medical device and controlling a movement of the medical device; and
a second communication module configured to exchange data with the portable operating unit.

2. The expansion unit according to claim 1, wherein said retaining device is configured to clamp said expansion unit from the underside of the portable operating unit to the portable operating unit.

3. The expansion unit according to claim 2, wherein said retaining device includes a displaceable lever to be fixed continuously adjustably in said retaining device and configured to affix the portable operating unit in the expansion unit.

4. The expansion unit according to claim 2, wherein said retaining device includes a displaceable lever with a spring balancer configured to affix the portable operating unit in the expansion unit.

5. The expansion unit according to claim 1, wherein an underside of the expansion unit is a flat surface.

6. The expansion unit according to claim 1, wherein said first communication module is configured to establish a Bluetooth connection or a WLAN connection.

7. The expansion unit according to claim 1, wherein said second communication module is connected via NFC or USB to the portable operating unit.

8. The expansion unit according to claim 1, which comprises an operating field facing a user during operation, which is embodied to project beyond the operating unit when the expansion unit is mechanically connected with the portable operating unit.

9. The expansion unit according to claim 8, wherein said operating field has a touchscreen.

10. The expansion unit according to claim 1, which comprises at least one button on said retaining device disposed for selective triggering by a user of the expansion unit using a hand that is holding the expansion unit.

11. A combination, comprising:
a medical device;
a flat portable operating unit being a tablet computer or a smartphone; and
a portable expansion unit for controlling functions of the medical device, the expansion unit including:
a retaining device to be adjusted to a size of the flat, portable operating unit, said retaining device being configured to mechanically connect the expansion unit detachably to the portable operating unit;
a first communication module configured to establish a data connection with the medical device enabling a user to control at least one function selected from the group consisting of triggering a release of radiation from the medical device and controlling a movement of the medical device; and
a second communication module configured to exchange data with the portable operating unit.

12. The combination according to claim 11, wherein said retaining device is configured to clamp said combination from the underside of the portable operating unit to the portable operating unit.

13. The combination according to claim 12, wherein said retaining device includes a displaceable lever to be fixed continuously adjustably in said retaining device and configured to affix the portable operating unit in the combination.

14. The combination according to claim 12, wherein said retaining device includes a displaceable lever with a spring balancer configured to affix the portable operating unit in the combination.

15. The combination according to claim 11, wherein said first communication module is configured to establish a Bluetooth connection or a WLAN connection.

16. The combination according to claim 11, wherein said second communication module is connected via NFC or USB to the portable operating unit.

17. The combination according to claim 11, which comprises an operating field facing a user during operation, which is embodied to project beyond the operating unit when the combination is mechanically connected with the portable operating unit.

18. The combination according to claim 17, wherein said operating field has a touchscreen.

19. The combination according to claim 11, which comprises at least one button on said retaining device disposed for selective triggering by a user of the combination using a hand that is holding the combination.

20. A method for operating a medical device, the method comprises providing the combination according to claim 11 and selectively triggering the medical device to release the radiation by way of said portable expansion unit.

* * * * *